(12) United States Patent
Waldenburg

(10) Patent No.: US 10,350,409 B2
(45) Date of Patent: Jul. 16, 2019

(54) INSTRUMENT FOR AND METHOD OF TREATING VENOMOUS BITES

(71) Applicant: Ottfried Waldenburg, Tucson, AZ (US)

(72) Inventor: Ottfried Waldenburg, Tucson, AZ (US)

( * ) Notice: Subject to any disclaimer, the term of this patent is extended or adjusted under 35 U.S.C. 154(b) by 263 days.

(21) Appl. No.: 15/059,262

(22) Filed: Mar. 2, 2016

(65) Prior Publication Data
US 2017/0021165 A1     Jan. 26, 2017

Related U.S. Application Data

(63) Continuation-in-part of application No. 14/671,835, filed on Mar. 27, 2015, now abandoned, which is a continuation-in-part of application No. 13/839,057, filed on Mar. 15, 2013, now abandoned.

(51) Int. Cl.
*A61N 1/32* (2006.01)
*A61N 1/20* (2006.01)
*A61F 7/02* (2006.01)

(52) U.S. Cl.
CPC ............. *A61N 1/326* (2013.01); *A61N 1/205* (2013.01); *A61N 1/32* (2013.01); *A61F 2007/0284* (2013.01)

(58) Field of Classification Search
CPC .......... A61N 1/326; A61N 1/32; A61N 1/205; A61F 2007/0284
See application file for complete search history.

(56) References Cited

U.S. PATENT DOCUMENTS

| | | | |
|---|---|---|---|
| 5,792,211 A * | 8/1998 | Teague | A61N 1/326 128/898 |
| 6,318,640 B1 | 11/2001 | Coffee | |
| 2008/0306436 A1* | 12/2008 | Edwards | A61M 5/19 604/67 |

OTHER PUBLICATIONS

U.S. Appl. No. 13/839,057, filed May 9, 2014, Office action.
U.S. Appl. No. 13/839,057, filed Sep. 30, 2014, Office action.
U.S. Appl. No. 14/671,835, filed Sep. 4, 2015, Office action.

* cited by examiner

*Primary Examiner* — Rex R Holmes
(74) *Attorney, Agent, or Firm* — John J. Connors; Connors & Assoc. pc

(57) ABSTRACT

A method and instrument for treating the toxic effect a patient experiences as a result of insect bites and snakebites comprises applying multiple instantaneous 20,000 to 30,000 volt electric discharges from a hand-operated piezoelectric device to a site of the bite.

1 Claim, 5 Drawing Sheets

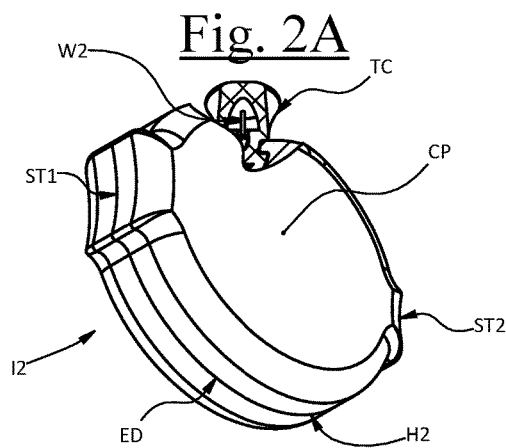
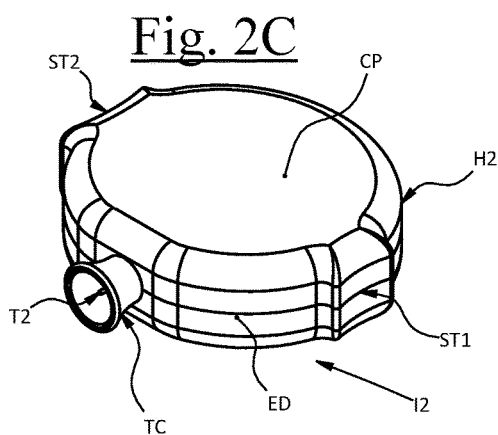
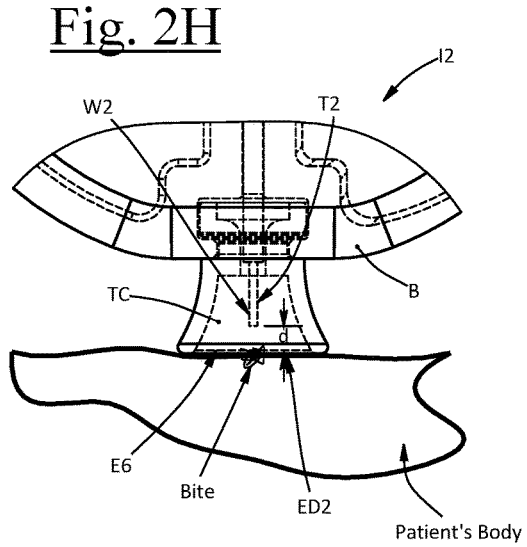
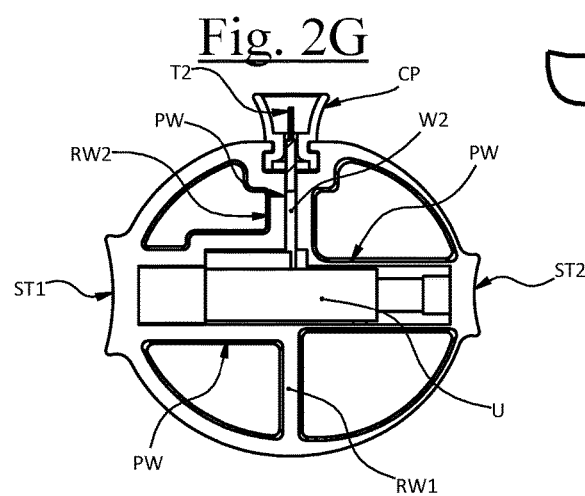

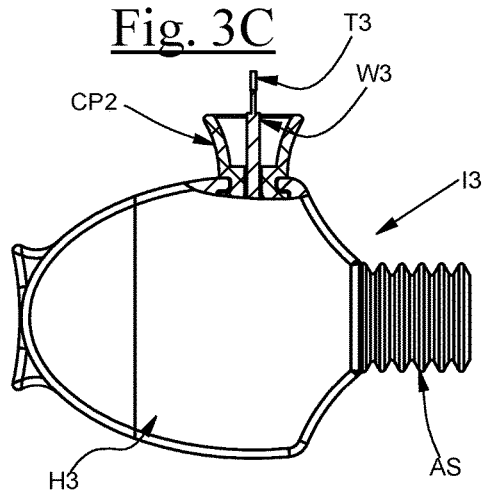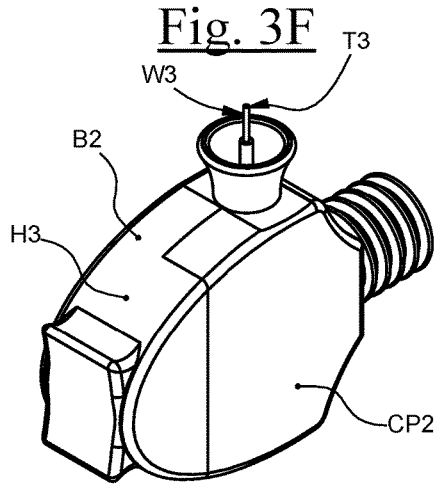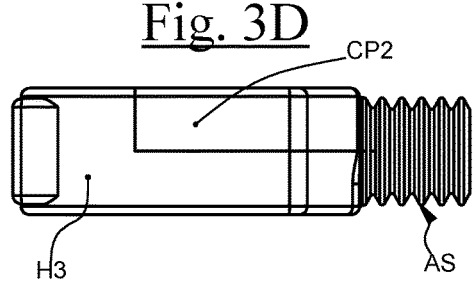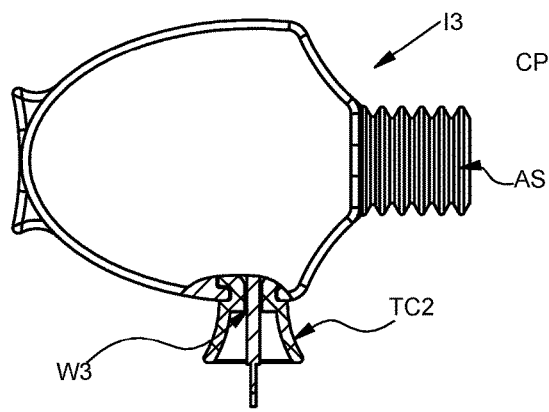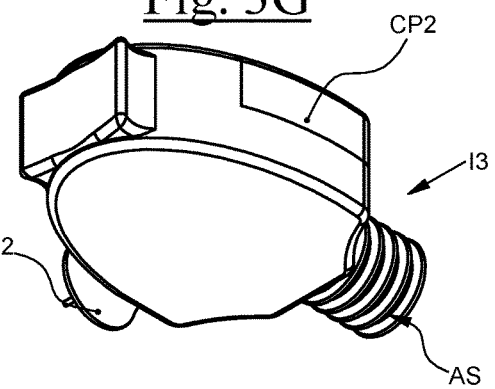

INSTRUMENT FOR AND METHOD OF TREATING VENOMOUS BITES

RELATED PATENT APPLICATIONS & INCORPORATION BY REFERENCE

This utility application is a continuation-in-part application of U.S. application Ser. No. 14/671,835, entitled "INSTRUMENT FOR AND METHOD OF TREATING VENOMOUS BITES," filed Mar. 27, 2015, now abandoned, which is a continuation-in-part application of U.S. application Ser. No. 13/839,057, entitled "METHOD OF TREATING VENOMOUS BITES," filed March 15, 2013, now abandoned; and this utility application claims the benefit under 35USC § 120 of these related applications that are incorporated herein by reference and made a part of this application, including any and all U.S. patents, U. S. patent applications, and other documents, hard copy or electronic, cited or referred to during the prosecution these related applications.

DEFINITIONS

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

The word "piezoelectricity" means electricity resulting from pressure.

The words "transparent" and "translucent" are equivalent.

BACKGROUND

Venomous bites from insects and snakes may be treated by an electrical discharge as discussed in U.S. Pat. No. 5,792,211 by Teague. Teague's instrument, however, cannot be comfortably grasped using only one hand and actuated using only the one hand grasping the instrument.

SUMMARY

My method and instrument are an improvement over Teague, and have one or more of the features depicted in the embodiments discussed in the section entitled "DETAILED DESCRIPTION OF SOME ILLUSTRATIVE EMBODIMENTS." These features are not listed in any rank order nor is this list intended to be exhaustive. The claims that follow define my instrument for and method of treating venomous bites, distinguishing them from the prior art; however, without limiting the scope of my instrument and method as expressed by these claims, in general terms, some, but not necessarily all, of their features are:

I have discovered that piezoelectricity may be used to treat successfully the toxic effect a patient experiences as a result of a venomous insect bite or a venomous snakebite by applying to a site of such a bite an instantaneous electric discharge from a hand-operated piezoelectric instrument that is isolated from ground during use and can be actuated using only the hand grasping the instrument.

In one embodiment, my instrument includes a housing, a barrel, and a handle sized and shaped to be gripped with one hand of a user. The housing contains a piezoelectric crystal held between two sections of a vice member. The barrel has a wire that extends lengthwise along the barrel and terminates at a tip that projects outward from the barrel. A trigger is positioned to be actuated by the index finger of a user while gripping the handle.

Thus, while a user holds the instrument by the handle with one hand and while gripping the trigger with an index finger of the one hand, the user depresses the trigger to actuate the mechanical linkage so that the two sections of the vice member apply pressure to the crystal to generate an electrical discharge at the tip. The user holds the tip directly on or adjacent the site of bite as the trigger is depressed.

In an alternate embodiment, the housing contains a piezoelectric unit having opposed ends and between these ends is the elongated wire. This wire extends outward from the piezoelectric unit and through the housing to terminate at a tip outward of the housing. The is electrically isolated from ground.

The housing comprises an elastic, resilient material and has opposed pressure sites that defect inward upon the application of pressure. One pressure site is nearby one opposed end of the piezoelectric unit and the other pressure site is nearby the other opposed end of the piezoelectric unit. Thus, the application of pressure to a pressure site results in pressure being applied to the piezoelectric unit, causing an instantaneous electric discharge at the wire's tip. The housing is configured to be held in the palm of the hand of a user between a thumb and a finger of the user, typically the index finger. Thus, pressing the thumb and finger towards each other deflects the elastic housing at the sites, to produce the instantaneous electric discharge from the tip. In another embodiment a rigid housing is used. Only one pressure site, for example, an accordion structure comprising a resilient material aligned with an end of the piezoelectric unit, is seated in an edge of the rigid housing. Compressing the accordion structure applies a force to the piezoelectric unit, resulting in a discharge at the wire's tip.

A tip cover may be used to avoid direct contact of the wire tip with the body of the patient. The tip cover is on the housing and the wire tip extends into the tip cover toward an open end of the tip cover. The tip cover is configured to be placed in contact with the body of a patient being treated for a venomous bite. The wire tip is rearward of the open end and is displaced generally from $\frac{1}{32}$ to $\frac{1}{16}$ inch from the body with the tip cover in contact with the patient's body and when the instantaneous electric discharge is applied to the site of the bite. Having the tip displace this small distance insure that a spark in generated between the tip and the bite. This appears to produce the best therapeutic treatment.

The embodiments illustrated are conveniently held in either the right or left hand of a user and operated using only this one hand.

DESCRIPTION OF THE DRAWING

Some embodiments of my method and instrument are discussed in detail in connection with the accompanying drawing, which is for illustrative purposes only. This drawing includes the following figures (FIGS.), with like numerals and letters indicating like parts:

FIG. 2A is a perspective view of the second embodiment shown in FIG. 2 looking at a portion of the bottom circumferential edge of the instrument with the instrument oriented substantially horizontally.

FIG. 2C is a perspective view of the second embodiment shown in FIG. 2 looking at a portion of the patient contact circumferential edge of the instrument with the instrument oriented substantially vertically.

FIG. 2G is a side view of the second embodiment shown in FIG. 2 with its cover plate removed.

FIG. 2H is a schematic view depicting the tip cover in contact with the body of a patient.

FIG. 3C is a side view of the third embodiment of my instrument shown in FIG. 3 showing the cover plate.

FIG. 3D is a plan view of the third embodiment of my instrument shown in FIG. 3.

FIG. 3E is a side view of the third embodiment of my instrument shown in FIG. 3 inverted to show the side opposite the cover plate.

FIG. 3F is a perspective view of the third embodiment of my instrument shown in FIG. 3 oriented substantially vertically and looking at a rear end.

FIG. 3G is a perspective view of the third embodiment of my instrument shown in FIG. 3 oriented substantially horizontally and looking at a rear end.

DETAILED DESCRIPTION OF SOME ILLUSTRATIVE EMBODIMENTS

General

My method treats the toxic effect a patient experiences as a result of an insect bite or a snakebite. It comprises applying to a site of the bite an instantaneous electric discharge, a spark. A hand-operated piezoelectric instrument is used in performing my method, for example, the instrument generally designated by the letter I (FIG. 1), the instrument generally designated by the letter I2 (FIGS. 2 through 2G), and the instrument generally designated by the letter I3 (FIGS. 3 through 3G). Anyone of these instruments 1, I2, and I3, upon actuation, generates a spark discharge at approximately of 20,000 to 30,000 volts, or greater. The voltage, however, is sufficiently low to avoid any injury to the patient. These embodiments of the instrument are sized to be hand held, manually operated, and electrically isolated from ground during use. The embodiments I2 and I3 include a housing that is held between the thumb and a finger, typically the index finger, of a user. The housing retains a conventional piezoelectric unit U that is actuated by pressing the thumb and finger towards each other to compress or flex the housing, or a portion thereof, to produce the spark applied to the bite.

FIG. 1

Figure 1:
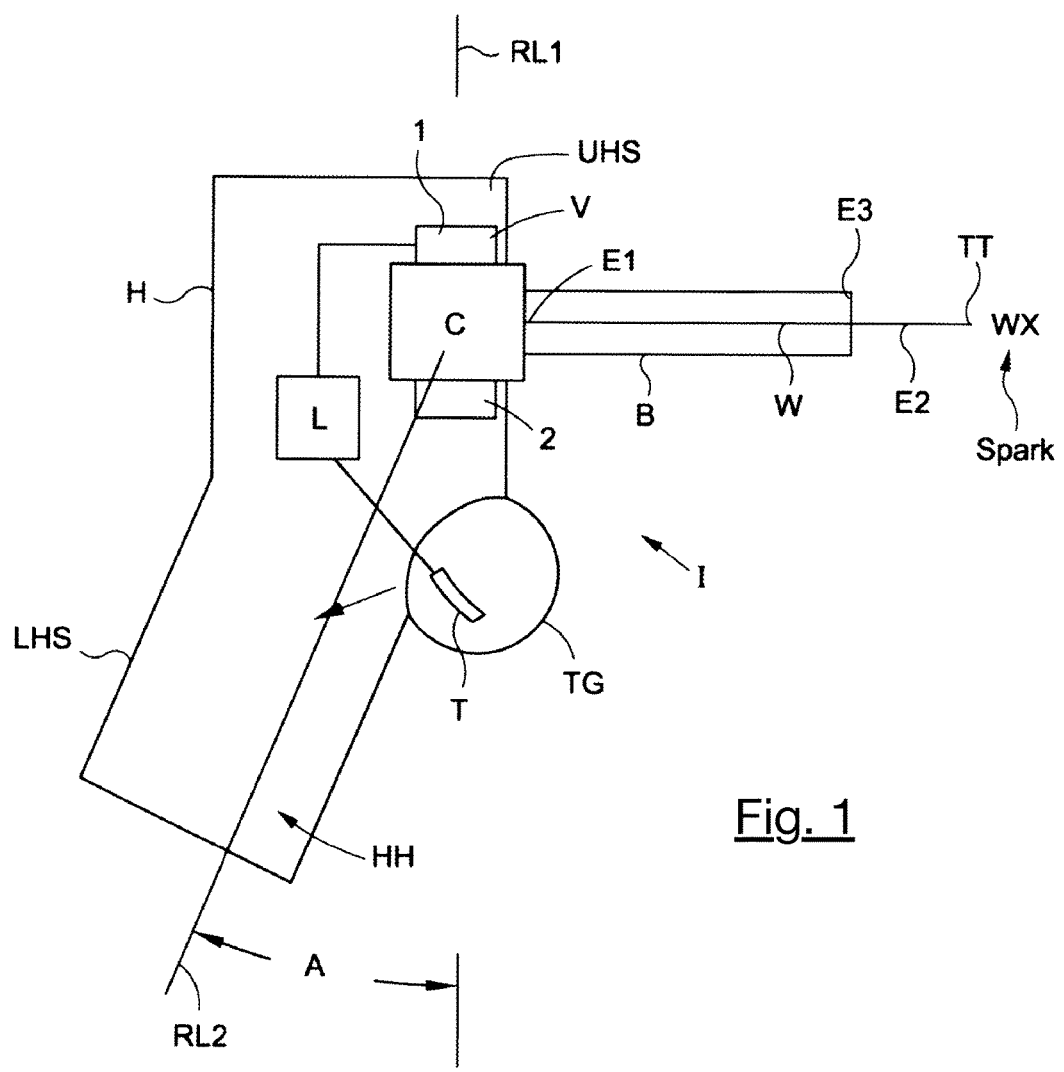
FIG. 1 is a schematic diagram of one embodiment of my instrument used in performing my method.

As depicted in FIG. 1, the instrument I includes a housing H having within it a piezoelectric crystal C held between two sections 1 and 2 of a vice V. The housing has an upper housing section UHS and a lower housing Section LHS, with the lower housing section configured as a handle HH that can be grasped by a user with one hand while being used to actuate a trigger T. A piezoelectric crystal C is within the upper housing section UHS. Extending at a right angle to a longitudinal reference line RL1 of the housing H is an elongated barrel B with a central, axial, electrically conductive wire W that extends lengthwise along the length of the barrel B. The respective relative positions of the handle HH and barrel may be defined by an angle A between the reference line RF1 and a reference line RF2 that intersects with the barrel B. For example, this angle A may be from 0 to 90 degrees.

One end E1 of the wire W is in electrical contact with the crystal C and the other end E2 of the wire projects from of the end E3 of the barrel. By actuating the trigger T, at the tip TT of the wire W a spark is created as current discharges therefrom and is applied directly to the site of the bite. The trigger T is located along an inner side of the handle HH at a position so the user, in the conventional manner of gripping a hand held pistol, can actuate the trigger by pulling the trigger with the index finger while simultaneously holding the handle. A trigger guard TG at least partially surrounds the trigger T, but allows the index finger to be wrapped around the trigger while the instrument I is being held. A mechanical linkage L operably connects the trigger T to the vice V. Upon manually actuating the trigger T by depressing it, the two sections 1 and 2 of the vice V apply pressure to the crystal C. This pressure, typically 2-3 pounds, causes the crystal C to discharge a current along the wire W. At the tip TT of the wire W a spark is created as current discharges. The handle HH and trigger T are made of material and connected in a manner that the instrument is electrically isolated from ground during use.

The instrument I is a convenient and simple tool to use in practicing my method. To practice my method, the site of the bite is first cleaned. While holding the handle HH with one hand and gripping the trigger T with an index finger, the tip TT of the wire W from which the spark is emitted is held directly on the site of the bite. The trigger T of the instrument I is manually actuated by the user to release a spark directly to the bite and the area surrounding the bite. Multiple instantaneous electric discharges are applied to a site of a bite spaced apart by approximately from 20 to 40 seconds. For example, approximately 8-15 treatment discharges are effect in most cases.

Figure 2:
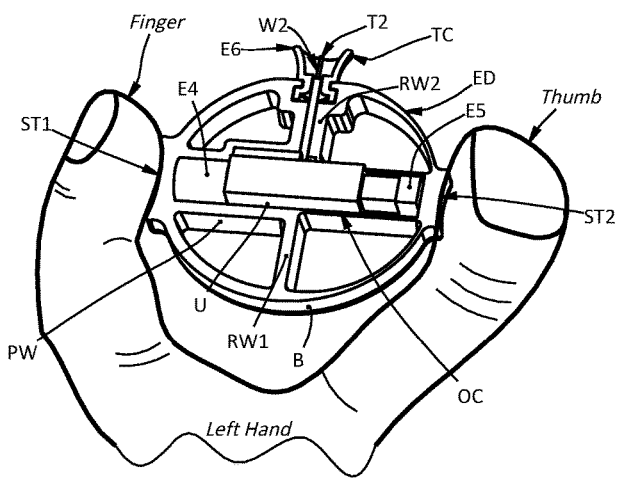
FIG. 2 is a perspective view of a second embodiment of my instrument being gripped between the thumb and finger of a user performing my method with a housing cover plate removed to show the interior of the housing.
Figure 2B:
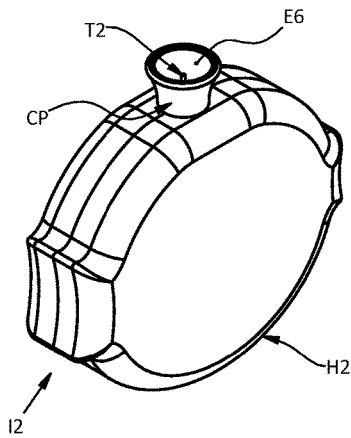
FIG. 2B is a perspective view of the second embodiment shown in FIG. 2 looking at a portion of a patient contact circumferential edge of the instrument with the instrument oriented substantially horizontally.
Figure 2D:
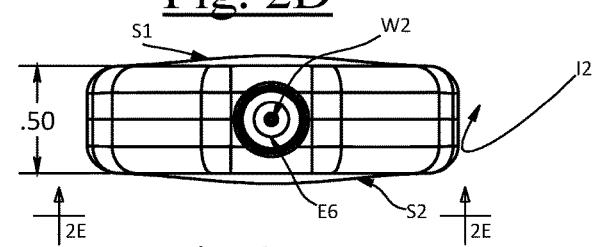
FIG. 2D is a plan view of the second embodiment shown in FIG. 2 taken along line 2D-2D of FIG. 2E.
Figure 3:
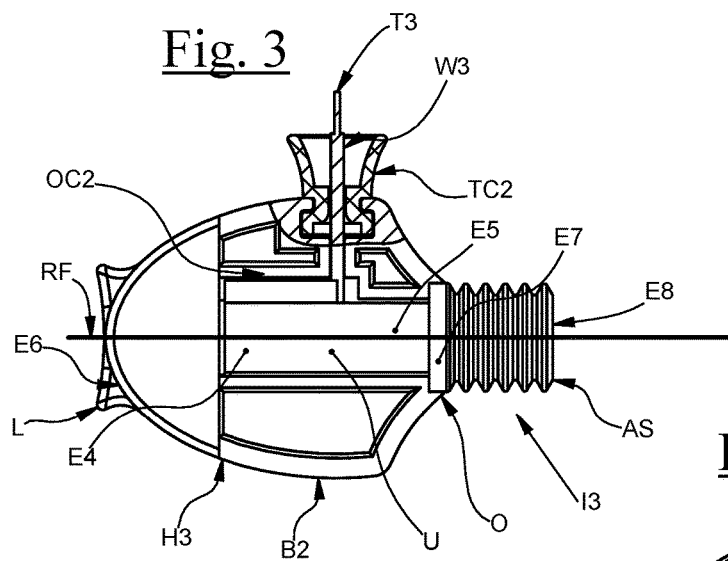
FIG. 3 is a side view of the third embodiment with its cover plate removed.
Figure 3A:
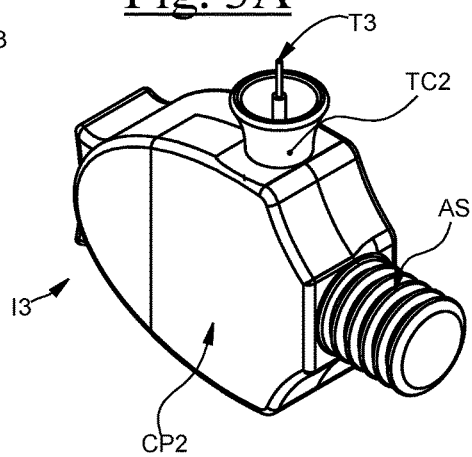
FIG. 3A is a perspective view of the third embodiment of my instrument shown in FIG. 3 oriented substantially vertically and looking at a forward end.
Figure 3B:
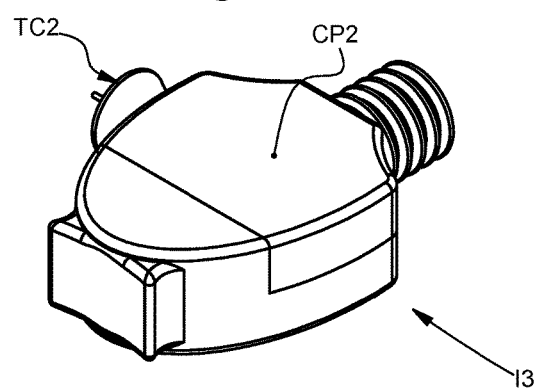
FIG. 3B is a perspective view of the third embodiment of my instrument shown in FIG. 3 oriented substantially horizontally.

FIGS. 2 through 2G

As illustrated in FIG. 2 the instrument I2 includes a housing H2 containing a conventional piezoelectric unit U. The housing H2 is made of an insulating material, for example, an elastic, resilient material such rubber. The entire housing maybe made of this material. Thus upon compression, the compressive force applied to the resilient material is transferred to the piezoelectric unit U, actuating this unit to produce the discharge.

The piezoelectric unit U has opposed ends E4 and E5, and between these ends is an elongated wire W2 that extends outward from the piezoelectric unit U and through the housing H2 to terminate at a tip T2 outward of the housing. The wire W2 is electrically isolated from ground. The housing H2 may be molded, for example, of rubber, and is configured to be held between a thumb and a finger of a user as depicted in FIG. 2. Thus, when the user presses his or her thumb and finger towards each other, the housing H2, or a portion thereof, is deflected inward to apply pressure to the piezoelectric unit U to produce an instantaneous electric discharge from the tip T2.

Figure 2E:
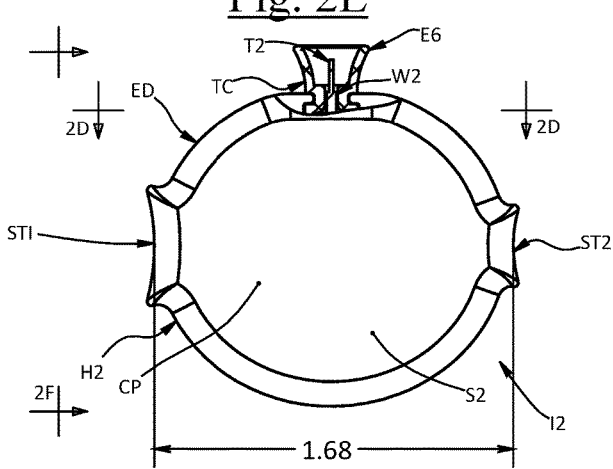
FIG. 2E is a side view of the second embodiment shown in FIG. 2 taken along line 2E-2E of FIG. 2D.
Figure 2F:
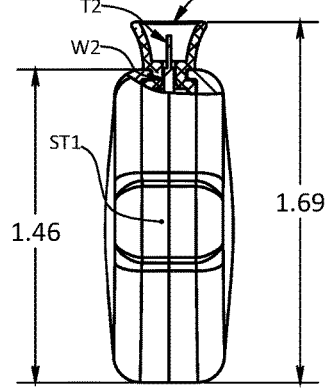
FIG. 2F a side view of the second embodiment shown in FIG. 2 taken along line 2F-2F of FIG. 2E.

In this second embodiment the housing H2 has a generally cylindrical shape comprising opposed flat sides S1 and S2 and a circular circumferential edge ED (FIGS. 2A and 2E). The housing H2 includes in its interior an open compartment OC disposed lengthwise along the diameter of the housing. Along the circumferential edge ED are opposed pressure sites ST1 and ST2 that defect inward upon the application of pressure. One site ST1 is nearby the one opposed end E4 of the piezoelectric unit U and the other site ST2 is nearby the other opposed end E5 of the piezoelectric unit, so that the application of pressure to either site results in pressure being applied to the piezoelectric unit U. In other words, the longitudinal axis of the piezoelectric unit U lies along the diameter of the housing upon inserting into the open compartment OC, and its ends E4 and E5 are, respectively, adjacent the sites ST1 and ST2. The distance between these sites ST1 and ST2 generally is from 1.0 to 4 inches. The thickness of the housing H2 generally is from 0.50 inch to 2 inches, and its height generally is from 0.50 inch to 2 inches.

The housing H2 includes a base B and a cover plate CP mounted to the base. It may be detachably connected or locked in position. Attaching the cover plate CP to the base forms the housing H2 retaining the piezoelectric unit U. As shown in FIGS. 2 and 2G, removal of the cover plate CP exposes the interior of the base B, enabling access to the open compartment OC defined by a pair parallel walls PW (FIG. 2). The open compartment OC is configured to hold the piezoelectric unit U snug within the compartment upon reattaching the cover plate CP to the base B. A pair of reinforcing walls RW1 and RW2 are used, one reinforcing wall R1 at a right angle to one of the pair parallel walls PW and the other reinforcing wall R2 at a right angle to the other of the pair parallel walls PW. The wire W2 extends from the piezoelectric unit U at a right angle to this unit and along a passageway PW (FIG. 2G) through the reinforcing wall R2 and from the housing H2 and into a tip cover TC.

The tip cover TC is on the exterior of housing and has an open end E6 and the tip T2 is inward of this open end. The tip cover, which may be transparent, has a generally truncated shape with a hollow interior into which the tip projects part way. An outer circular edge ED2 of the tip cover TC is configured to be placed in contact with a body of a patient being treated for a venomous bite and surrounding the bite. Thus, with the edge ED2 of the Tip cover TC in contact with the patient's body, the tip T2 is a distance d (FIG. 2H) $\frac{1}{32}$ to $\frac{1}{16}$ inch from the patient's body when the instantaneous electric discharge is emitted from the tip.

FIGS. 3 through 3G

The instrument 13 illustrated in FIGS. 3 through 3G is similar to the instrument 12 having a housing H3 in which the piezoelectric unit U is retained in an open compartment OC2 (FIG. 3) that is closed when a cover plate CP2 is attached to a base B2. The housing H3 has a generally oval or oblong shape, and the piezoelectric unit U is oriented along the longitudinal axis or center reference line RF (FIG. 3) of the base B2. The base B2 is formed from a rigid, insulting material such as a plastic.

As shown in FIG. 3, one end E6 of the base B2 has an exterior land L identifying where a thumb of finger of a user may be placed when grasping the instrument 13. Opposite the end E6 is an opening O in the base B2. A rubber compression member in the form of a cylindrical accordion structure AS is inserted into the opening O and oriented along the longitudinal axis of the base B2 in alignment with the piezoelectric unit U. An inner end E7 (FIG. 3) of the accordion structure AS is adjacent the end E5 of the piezoelectric unit U. In essentially the same manner as discussed above in connection with instrument 12, actuation of the piezoelectric unit U produces an electrical discharge at a tip T3 of a wire W3 projecting at a right angle from the piezoelectric unit U into a tip cover TC2.

In operation, a user grips the instrument in a manner similar to that depicted in FIG. 2 with a finger or thumb on the land L and a finger or thumb on an end E8 of the accordion structure AS. To produce an electrical discharge at the tip T3 of the wire W3 with the tip cover TC2 pressed against the patient's body like that shown in FIG. 2H, the user compresses the accordion structure AS to apply pressure to the end E5 and actuate the piezoelectric unit U to produce an electrical discharge from the tip. In this embodiment only the accordion structure AS is compressed; the land L is not. This is in contrast to the instrument 12 where the entire housing H2 is made of an elastic, resilient material material

SCOPE OF THE INVENTION

The above presents a description of the best mode I contemplate of carrying out my method, and of the manner and process of making and using it, in such full, clear, concise, and exact terms as to enable a person skilled in the art to make and use. My method is, however, susceptible to modifications and alternate constructions from the illustrative embodiment discussed above which are fully equivalent. Consequently, it is not the intention to limit my method to the particular embodiment disclosed. On the contrary, my intention is to cover all modifications and alternate constructions coming within the spirit and scope of my method as generally expressed by the following claims, which particularly point out and distinctly claim the subject matter of my invention:

The invention claimed is:

1. An instrument for treating a venomous bite including
a housing containing a piezoelectric unit having opposed ends and between said ends an elongated wire that extends outward from the piezoelectric unit and through the housing to terminate at a tip outward of the housing,
said housing having opposed pressure sites, one site nearby one opposed end of the piezoelectric unit and the other site nearby the other opposed end of the piezoelectric unit, at least on site defecting to apply pressure to and actuate the piezoelectric unit,
said housing comprising an elastic material and configured to be held in the palm of the hand of a user between a thumb and a finger of a user and contact the said one site, whereby pressing the thumb and finger towards each other to deflect the housing, or a portion thereof, produces an instantaneous electric discharge from said tip,
a tip cover on the housing into which the tip of the wire extends toward an open end of the tip cover, said tip being inward of the open end,
said tip cover configured to be placed in contact with a body of a patient being treated for a venomous bite, so that, with the tip cover in contact with the patient's body, said tip is 1/32 to 1/16 inch from said patient's body when the instantaneous electric discharge is emitted from said tip, the housing is made of an insulating material and wire is electrically isolated from ground, and where the tip cover is transparent.

* * * * *